United States Patent
Takada et al.

(10) Patent No.: US 6,552,082 B2
(45) Date of Patent: Apr. 22, 2003

(54) SOLUTION OF N-[O-(P-PIVALOYLOXYBEN-ZENESULFONYLAMINO)BENZOYL] GLYCINE MONOSODIUM SALT TETRA-HYDRATE AND DRUG PRODUCT THEREOF

(75) Inventors: Akira Takada, Mishima-gun (JP); Masao Sudoh, Mishima-gun (JP)

(73) Assignee: Ono Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 09/882,335

(22) Filed: Jun. 18, 2001

(65) Prior Publication Data
US 2002/0022738 A1 Feb. 21, 2002

(30) Foreign Application Priority Data
Jun. 29, 2000 (JP) .................. 2000-195852
Jun. 29, 2000 (JP) .................. 2000-195853

(51) Int. Cl.$^7$ .................. A61K 31/195; C07C 31/00
(52) U.S. Cl. .................. 514/562; 560/13
(58) Field of Search .................. 560/13; 514/562

(56) References Cited

U.S. PATENT DOCUMENTS

| | | | |
|---|---|---|---|
| 5,017,610 A | 5/1991 | Imaki et al. | |
| 5,336,681 A | 8/1994 | Imaki et al. | |
| 5,359,121 A | 10/1994 | Imaki et al. | |
| 5,403,850 A | 4/1995 | Imaki et al. | |

FOREIGN PATENT DOCUMENTS

| | | |
|---|---|---|
| EP | 0347168 | 12/1989 |
| EP | 0539223 | 4/1993 |
| JP | 3020253 | 1/1991 |
| JP | 5194366 | 3/1993 |
| JP | 5194366 | 8/1993 |
| JP | 9040692 | 2/1997 |
| WO | 0015207 | 3/2000 |

*Primary Examiner*—Johann Richter
*Assistant Examiner*—Paul A. Zucker
(74) *Attorney, Agent, or Firm*—Stevens, Davis, Miller & Mosher, L.L.P.

(57) ABSTRACT

A solution of N-[o-(p-pivaloyloxybenzenesulfonylamino) benzoyl]glycine monosodium salt tetra-hydrate (I) comprising at least one pH adjuster selected from tri-sodium phosphate, a hydrate thereof, sodium hydroxide or potassium hydroxide and a drug product using the solution. According to the invention, the solubility of the compound (I) increases and thereby it is possible to provide a solution thereof and a drug product using it. Moreover, by using a mixture of water and an organic solvent, greatly improved solubility makes it possible to manufacture a solution of higher concentration of the compound (I), and high-dosage drug products using it.

15 Claims, 1 Drawing Sheet

[Figure 1]
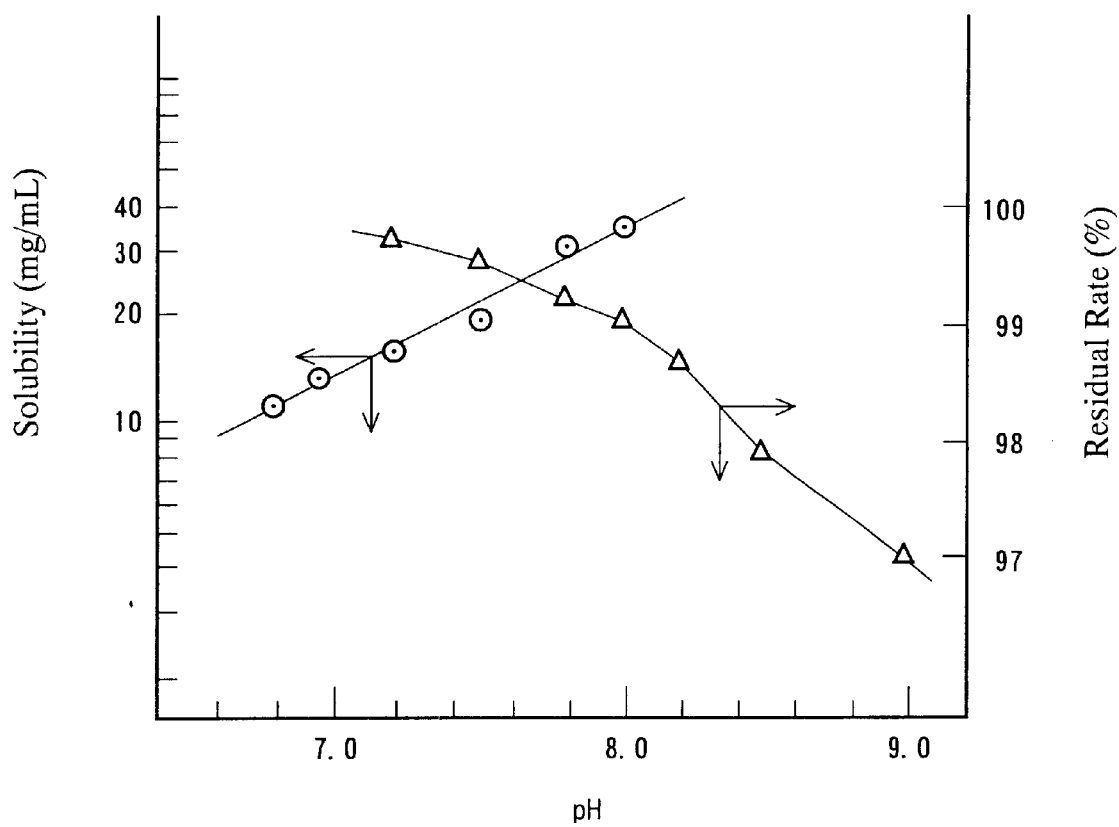

SOLUTION OF N-[O-(P-PIVALOYLOXYBEN-ZENESULFONYLAMINO)BENZOYL] GLYCINE MONOSODIUM SALT TETRA-HYDRATE AND DRUG PRODUCT THEREOF

TECHNICAL FIELD

The present invention relates to a solution of N-[o-(p-pivaloyloxybenzenesulfonylamino)benzoyl]glycine monosodium salt tetra-hydrate of formula (I)

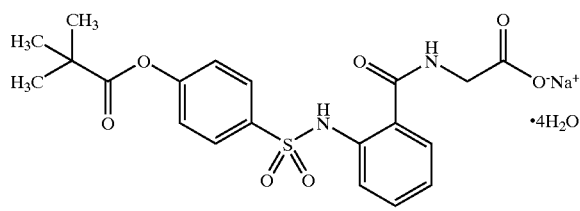

(I)

comprising a specific pH adjuster, and a drug product using the solution.

BACKGROUND ART

As to the compound used in the present invention, a free compound thereof, i.e. N-[o-(p-pivaloyloxybenzenesulfonylamino)benzoyl]glycine of formula (II)

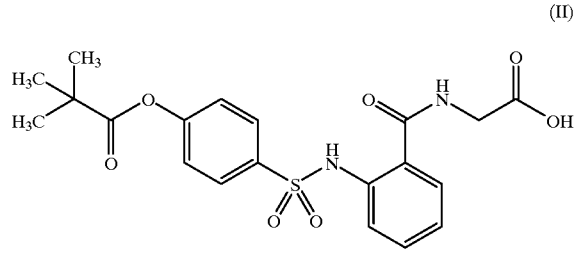

(II)

is described in example 2 (63) of JP kokai hei 3-20253 (i.e. EP 0 347 168) and a monosodium salt tetra-hydrate thereof, i.e. the compound of formula (I) is described in example 3 of JP kokai hei 5-194366 (i.e. EP 0 539 223) and reference example of JP kokai hei 9-40692 (no EP publication).

The compound (I) has an inhibitory activity against elastase and is a very useful compound which is expected to be used for the treatment of acute pulmonary disorders etc. Since those patients suffering from acute pulmonary disorders are in a serious condition, it is necessary to administer a drug parenterally, preferably as an injection for a long time (from 24 hours to several days) continuously. Therefore the compound (I) is preferably formulated as an injection or a solid composition to be dissolved before administration, more preferably formulated as a freeze-dried drug product.

However, the solubility of the compound (I) in water is less than 0.4 mg/mL and its solubility in ethanol is less than 6 mg/mL, and so it was hard to prepare a clear solution thereof for injection using normal solvents.

On the other hand, JP kokai hei 9-40692 discloses a method for the preparation of the compound (I) by suspending a compound of formula (II) to a mixture of water and ethanol, adding sodium hydroxide thereto and heating and then cooling. This operation shows a method for the preparation of a sodium salt tetra-hydrate from a free carboxylic form of formula (II) but does not intend to improve the solubility of sodium salt tetra-hydrate of formula (I).

DISCLOSURE OF INVENTION

The object of the present invention consists in improving the solubility of the compound (I), and thereby providing a solution thereof and some kinds of drug products using the solution, moreover providing a solution of higher concentration and a high-dosage drug product using the solution.

Considering the effective dose of the compound (I) and the volume of suitable closed containers (vials, ampoules, etc.), the required solubility of the compound (I) is estimated to be more than 15 mg/mL.

As a result of energetic investigations in order to improve the solubility of the compound (I), surprisingly, the present inventors have found that the purpose was accomplished by adding at least one pH adjuster selected from tri-sodium phosphate, a hydrate thereof, sodium hydroxide or potassium hydroxide to the solution.

As a result of another investigation to obtain a solution of higher concentration of the compound (I), the object is accomplished by using a kind of organic solvent except water in addition to using pH adjusters.

That is, the present invention relates to a solution of N-[o-(p-pivaloyloxybenzenesulfonylamino)benzoyl]glycine monosodium salt tetra-hydrate of formula (I)

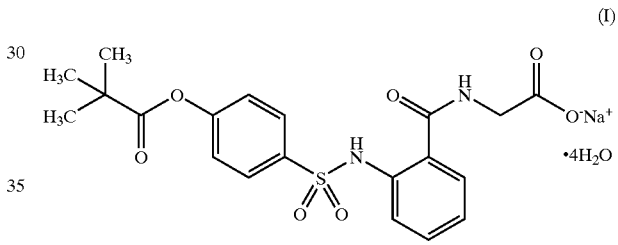

(I)

comprising at least one pH adjuster selected from tri-sodium phosphate, a hydrate thereof, sodium hydroxide or potassium hydroxide and a drug product using the solution.

More particularly, the present invention relates to a solution of N-[o-(p-pivaloyloxybenzenesulfonylamino)-benzoyl]glycine monosodium salt tetra-hydrate of formula (I) comprising at least one pH adjuster selected from tri-sodium phosphate, a hydrate thereof, sodium hydroxide or potassium hydroxide in which the solvent is exclusively water, a solution wherein the solvent is a mixture of water and an organic solvent or a novel drug product using the solution optionally comprising excipients.

Besides, the present invention includes a novel freeze-dried drug product comprising the compound (I) and at least one pH adjuster selected from tri-sodium phosphate, a hydrate thereof, sodium hydroxide or potassium hydroxide.

As the present inventors first considered that the solubility of the compound (I) was greatly subject to the pH of the solution, the relationship between the solubility and pH was investigated.

On the other hand, since the compound (I) has an ester bond in its structure and it was assumed to be unstable in a basic aqueous solution, the present inventors investigated the influence of pH on the stability of the compound (I) at the same time.

(1) The Measurement of Solubility and Stability

Aqueous solutions of di-sodium hydrogen phosphate and tri-sodium phosphate were mixed in various ratios to prepare buffers of various pH. To the prepared buffers was added sodium chloride in order to fix the ionic strength of the buffers to be 0.2. At 25 degrees Centigrade condition, to each buffer was added the compound (I), and then according to the method of solubility test of Japan pharmacopoeia, a saturated solution was prepared by stirring for 30 seconds every 5 minutes for 30 minutes. Each solution was centrifuged and the supernatant was filtrated. The concentration of the filtrate was calculated by liquid chromatography and was defined as the solubility (mg/mL) and the measured value was defined as the initial value of the stability test. The results of measurement of the solubility are shown in FIG. 1 (open circles in the figure).

After each filtrate was incubated at 25 degrees Centigrade for eight hours, the residual rates, or amount of residue as a percentage, of the compound (I) were measured by liquid chromatography. The residual rate after eight hours was defined as the parameter for judging the stability. The results are shown in FIG. 1 (triangles in the figure).

FIG. 1 shows that the higher the pH is, the better the solubility of the compound (I) is, while it shows that the higher the pH is, the more decomposed the compound is. Therefore in order to use the compound (I) as a pharmaceutical product, it is necessary to keep it in the optimal range of pH in terms of solubility and stability.

That is, in terms of solubility, the solution should remain clear without eduction of the compound (I); on the other hand in terms of stability, the residual rate must be more than 98% that is acceptable for pharmaceuticals. It proved that the optimal range of pH for the condition was between 7.0 and 8.5 from FIG. 1.

On the other hand, the specification of JP kokai hei 5-194366 discloses a drug product given by admixing N-[o-(p-pivaloyloxybenzenesulfonylamino)benzoyl]glycine monosodium salt tetra-hydrate (10 g), distilled water (500 mL), sodium chloride (7 g) and sodium carbonate (anhydrous) (1.5 g), filled 5 mL portion into each vial and freeze-dried by a conventional method.

However, it proved that the pH of the freeze-dried product manufactured according to the formulation example was ascended in the time course and gave a large amount of a decomposition product. The results are shown below.

(2) The Change of pH in the Time Course on Freeze-dried Product of the Compound (I) Comprising Sodium Carbonate The pH was measured on aqueous solutions prepared by admixing each component in the ratios described in the above specification of JP kokai hei 5-194366 at the following three points.

(a) when the aqueous solution was prepared,
(b) when the prepared aqueous solution was filled in each vial (5 mL), freeze-dried and then dissolved in water (10 mL),
(c) when the prepared aqueous solution was filled in each vial (5 mL), freeze-dried and the formulation obtained was left at 60 degrees Centigrade for two weeks and dissolved in water (10 mL).

The result was that the pH was (a) 7.80, (b) 8.11 and (c) 8.44.

When the freeze-dried product was left at 60 degrees Centigrade for two weeks, the residual rate of the compound (I) was 91.4%.

These results show that addition of sodium carbonate in the formulation ascends the pH in the time course and long-term storage accelerates the decomposition of the compound (I) though the pH was in the range between 7.0 and 8.5, which we assumed optimal.

Sodium bicarbonate and potassium carbonate in place of sodium carbonate also ascended the pH in the time course and accelerated the decomposition.

As shown above, even if an aqueous solution of the compound (I) has an adequate solubility manufactured by adjusting to the optimal pH ranges, it is harmful if the drug product thereof is decomposed by ascending pH during storage.

Therefore the present inventors have energetically made efforts to find a pH adjuster which was capable of adjusting to the optimal pH range which gave more than a standard solubility and keeping the pH almost equal to the pH after the aqueous solution was prepared during the storage of the drug product thereof.

(3) The Investigation of pH Adjusters

The present inventors have investigated the amounts of di-sodium hydrogen phosphate, tri-sodium phosphate, potassium hydroxide and sodium hydroxide to add and the changes in pH thereby.

(i) Di-sodium Hydrogen Phosphate

Mannitol (8 g) was dissolved in water (50 mL) and thereto was suspended the compound (I) (4 g). Di-sodium hydrogen phosphate dodecahydrate (80 g) was added to water (200 mL) and dissolved by heating. To the above suspension under stirring with a stirrer was added the aqueous solution of Di-sodium hydrogen phosphate dodecahydrate by 5 mL each and the pH was measured. The results are shown in table 1.

The suspension of the compound (I) did not turn into a clear aqueous solution even when the pH was adjusted to 8.18 by adding the aqueous solution of di-sodium hydrogen phosphate dodecahydrate (200 mL), i.e. 80 g of di-sodium hydrogen phosphate dodecahydrate.

(ii) Tri-sodium Phosphate

Mannitol (8 g) was dissolved in water (140 mL) and to the solution was suspended the compound (I) (4 g). To the suspension under stirring with a stirrer was added an aqueous solution of tri-sodium dodecahydrate (4 g/100 mL) by 5 mL portion each and the pH was measured. The results are shown in table 1.

The suspension turned into a clear aqueous solution when 45 mL of the aqueous solution of tri-sodium phosphate dodecahydrate was added, and the pH of the solution was 7.19.

(iii) Potassium Hydroxide

Mannitol (8 g) was dissolved in water (180 mL) and to the mixture was suspended the compound (I) (4 g). To the suspension under stirring with a stirrer was added 1N aqueous solution of potassium hydroxide (0.5 mL portion each) and the pH of the solution was measured. The results are shown in table 2.

The suspension turned into a clear aqueous solution when 5 mL of the aqueous solution of potassium hydroxide was added, and the pH of the solution was 7.20.

(iv) Sodium Hydroxide

The compound (I) (7.5 g) was suspended to water (400 mL). To the suspension under stirring with a stirrer was added 1N aqueous solution of sodium hydroxide (1 mL portion each) and the pH was measured. The results are shown in table 2.

The suspension turned into a clear aqueous solution when 7 mL of the aqueous solution of sodium hydroxide was added, and the pH was 7.44.

TABLE 1

| Amount (mL) | pH (i) di-sodium hydrogen phosphate | (ii) tri-sodium phosphate |
|---|---|---|
| 0 | 6.83 | 6.10 |
| 5 | 7.28 | 6.22 |
| 10 | 7.46 | 6.30 |
| 15 | 7.60 | 6.45 |
| 20 | 7.68 | 6.57 |
| 25 | 7.75 | 6.66 |
| 30 | 7.81 | 6.73 |
| 35 | 7.85 | 6.79 |
| 40 | 7.89 | 6.91 |
| 45 | 7.92 | 7.19 |
| 50 | 7.94 | 7.57 |
| 55 | 7.97 | 7.93 |
| 60 | 7.99 | 8.34 |
| 65 | 8.01 | 8.95 |
| 70 | 8.03 | 10.10 |
| 80 | 8.06 | — |
| 90 | 7.93 | — |
| 100 | 7.94 | — |
| 150 | 8.06 | — |
| 200 | 8.18 | — |

TABLE 2

| Amount (mL) | pH (i) potassium hydroxide | (ii) sodium hydroxide |
|---|---|---|
| 0 | 6.34 | 6.94 |
| 0.5 | 6.32 | — |
| 1.0 | 6.36 | 7.06 |
| 1.5 | 6.39 | — |
| 2.0 | 6.53 | 7.14 |
| 2.5 | 6.64 | — |
| 3.0 | 6.76 | 7.18 |
| 3.5 | 6.86 | — |
| 4.0 | 6.97 | 7.22 |
| 4.5 | 7.08 | — |
| 5.0 | 7.20 | 7.26 |
| 5.5 | 7.36 | — |
| 6.0 | 7.65 | 7.32 |
| 6.5 | 8.06 | — |
| 7.0 | 8.45 | 7.44 |
| 7.5 | 9.42 | — |
| 8.0 | — | 7.59 |
| 9.0 | — | 7.78 |
| 10 | — | 7.97 |
| 11 | — | 8.21 |
| 12 | — | 8.55 |
| 13 | — | 9.27 |

From the results above, di-sodium hydrogen phosphate could provide optimal pH, but could not give a clear solution though a large amount was added. Therefore it was judged that di-sodium hydrogen phosphate was not a suitable pH adjuster which could accomplish the purpose of the present invention.

On the other hand, for the preparation of a solution, by using tri-sodium phosphate dodecahydrate, potassium hydroxide and sodium hydroxide, optimal pH were obtained immediately and a clear solution having more than a standard solubility could be manufactured.

The following experiments (4) to (9) were performed, regarding the three pH adjusters which could accomplish the object by the above experiment.

(4) Stability of the Drug Products

Mannitol (8 g) was dissolved in water (150 mL) and thereto was suspended the compound (I) (4 g). To the suspension was added one pH adjuster selected from the following (i)~(iii), and finally the solution was filled up to 200 mL in total by water to obtain a clear solution.

(i) an aqueous solution of tri-sodium phosphate dodecahydrate (36.4 mg/mL; 50 mL), (ii) an aqueous solution of potassium hydroxide (56 mg/mL 6 mL), (iii) an aqueous solution of sodium hydroxide (40 mg/mL; 5.6 mL)

The pH of the prepared clear aqueous solutions was measured at the following three points.

(a) when the aqueous solutions were prepared, (b) when the prepared aqueous solutions were filled in each vial (5 mL), freeze-dried and then dissolved in water (10 mL), (c) when the prepared aqueous solution was filled in each vial (5 mL), freeze-dried and the drug product was left at 60 degrees Centigrade for two weeks (in case of sodium hydroxide for one month) and dissolved in water (10 mL).

The results are shown in table 3.

TABLE 3

|  | (a) | (b) | (c) |
|---|---|---|---|
| (i) tri-sodium phosphate | 7.75 | 7.75 | 7.73 |
| (ii) potassium hydroxide | 7.81 | 7.86 | 7.86 |
| (iii) sodium hydroxide | 7.90 | 7.92 | 7.90 |

Furthermore, when the freeze-dried product manufactured by adding sodium hydroxide was left at 60 degrees Centigrade for 1 month, the residual rate of the compound (I) was 98.3%.

From the results shown above, the drug products of the compound (I) comprising tri-sodium phosphate, potassium hydroxide or sodium hydroxide proved to be excellent in that the pH of the aqueous solution of the compound (I) could be fixed without ascending the pH in the time course and the compound (I) was stable during storage for a certain period.

Next the same investigation was performed on amino acid compounds, tris(hydroxymethyl)aminomethane and meglumine which were used for the same purpose as pH adjusters.

(5) Investigation of Compounds which can be Replaced with pH Adjusters

When KYORYOKU MORIAMINE infusion (Brand Name; manufactured by Morishita Roussel) as an amino acid compound was admixed with the compound (I) (5 mg/mL), great change of pH was not found (pH 6.36 after preparation and pH 6.13 after twenty-four hours), but the decomposition of the compound (I) was accelerated and the residual rate of the compound (I) after twenty-four hours was 54.1%. From these results it was judged that amino acid compounds were not suitable for admixing with the compound (I).

On the other hand, tris(hydroxymethyl)aminomethane lowered the stability of freeze-dried product; meglumine had the problem of lowering the stability during storage and discoloration.

From the results above, it was confirmed that in order to maintain a good solubility and stability not only just after preparation of the solution but also for a long term after manufacturing the drug product, not all pH adjusters which could adjust to suitable pH ranges might do, but exclusively tri-sodium phosphate, a hydrate thereof, sodium hydroxide and potassium hydroxide could accomplish the purpose.

Moreover, the present inventors aimed to manufacture a solution of higher concentration of the compound (I) than the above solution whose solubility was around 20 mg/mL, and a higher-dosage drug product using it.

(6) Investigation of a Solution of High Concentration (i) To water (3 mL) were added the compound (I) (400 mg) and mannitol (100 mg). To the mixture under stirring, was added IN aqueous solution of sodium hydroxide (0.6 mL: corresponds to 24 mg). Thereto was added water in order to fill up to 5 mL of total amount. However, the mixture did not turn into a clear solution but a white suspension. Therefore it was impossible to freeze-dry the suspension.

Hereby it was found that the improvement of solubility using specific pH adjusters was limited, and so the present inventors next paid attention to the kinds of solvent.

(ii) To a mixture of ethanol (1.0 mL) and water (total approximately 3 mL) was suspended the compound (I) (400 mg) and mannitol (100 mg) and to the mixture under stirring was added 1N aqueous solution of sodium hydroxide (0.6 mL; corresponds to 24 mg) little by little. Thereto was added water in order to fill up to 5 mL of total amount, to give a clear solution.

As shown above, in addition to using pH adjusters, use of a mixture of water and an organic solvent served to improve the solubility of the compound (I) to a great degree, thereby to manufacture a solution of higher concentration.

On the other hand, in order to formulate the solution of the present invention to an injection, particularly to a freeze-dried product, the amount of organic solvent is limited in the formulation process. That is to say, the capacity of normally used freeze-drying machine to cool is up to around −50 degrees Centigrade. Around −50 degrees Centigrade the ratio of organic solvent to the total amount is over 40%, when the mixture is subject to freeze-drying, it is in danger of bumping. Therefore, the amount of an organic solvent to add must be limited less than around 40% of the total solution.

Considering the above fact, optimal amount of the organic solvent was investigated.

(7) The Investigation of the Amount of the Organic Solvent

To a mixture of ethanol (the amount shown in the following table) and water (total approximately 3 mL) were suspended the compound (I) (400 mg) and mannitol (100 mg), and to the mixture under stirring was added 1N aqueous solution of sodium hydroxide (0.6 mL; corresponds to 24 mg) little by little. To the mixture was added water in order to fill up to 5 mL of total solution. The measured results of the conditions of the solutions manufactured according to the present prescription and the pH are shown in table 4.

TABLE 4

| Ethanol (mL) | Results | pH |
|---|---|---|
| 0.00 | The solute remained | — |
| 0.05 | Clear solution | 7.04 |
| 0.25 | Clear solution | 8.08 |

TABLE 4-continued

| Ethanol (mL) | Results | pH |
|---|---|---|
| 0.50 | Clear solution | 8.13 |
| 0.75 | Clear solution | 8.18 |
| 1.00 | Clear solution | 8.22 |
| 1.50 | Clear solution | 8.36 |
| 2.00 | Clear solution | 8.49 |

Hereby the present inventors succeeded in obtaining a solution of very high concentration by using ethanol for 1~40 v/v % of total solvent amount in the presence of a certain amount of sodium hydroxide.

On the other hand, the amount of pH adjusters and its stability of the compound (I) were examined.

(8) To a mixture of ethanol (1.25 mL) and water (total approximately 3 mL) was suspended the compound (I) (400 mg) and mannitol (100 mg) and to the mixture under stirring was added 1N aqueous solution of sodium hydroxide (the amount shown in the following table) little by little. To the mixture added water in order to fill up to 5 mL of total solution. The conditions of the solution prepared according to the present prescription, pH and the measured results of the residual ratio of the compound (I) by liquid chromatography after leaving at 25 degrees Centigrade for 8 hours are shown in table 5.

TABLE 5

| sodium hydroxide (mg) | Results | pH | Residual Rate (%) |
|---|---|---|---|
| 15 | Solute remained | — | — |
| 16 | Clear solution | 7.86 | — |
| 18 | Clear solution | 7.96 | — |
| 20 | Clear solution | 8.12 | 99.7 |
| 22 | Clear solution | 8.20 | — |
| 24 | Clear solution | 8.32 | 99.2 |
| 25 | Clear solution | 8.26 | — |
| 26 | Clear solution | 8.49 | 98.9 |
| 27 | Clear solution | 8.52 | 98.7 |
| 28 | Clear solution | 8.75 | 98.5 |

From the results shown above, it was possible to give an optimal pH by using pH adjusters in the presence of a certain amount of an organic solvent as well as the solution of the pound (I) comprising exclusively water as a solvent.

Even though the pH was over 8.5, the residual rate of the compound (I) was kept over 98%, aside from the solution of the pound (I) comprising exclusively water as a solvent.

As shown above, it is entirely surprising that the solubility of the compound (I) is improved to a great degree and the stability is also improved even in high pH ranges, by using an organic solvent; i.e. a mixture of water and an organic solvent in addition to pH adjusters and the fact was found out for the first time.

Hereby the stability of the freeze-dried drug product using the solution of high concentration of the present invention was examined.

(9) (i) the clear solution using ethanol 1 mL in the above (7) and (ii) the clear solution using the sodium hydroxide 27 mg in the above (8) were sterilized by a conventional method, filled to vials, and freeze-dried by a conventional method to give vials each containing 400 mg of the compound (I). The solubility in the time course was measured. The results are shown in table 6.

TABLE 6

| | Solution (i) | | Solution (ii) | |
|---|---|---|---|---|
| Storage Condition | Residual Rate | pH | Residual Rate | pH |
| When the freeze-dried product was manufactured | 99.5% | 8.26 | 98.7% | 8.26 |
| 60 degrees Centigrade, 1 month | 99.5% | 8.25 | 98.1% | 8.25 |

As shown in table 6, it was found that the freeze-dried drug product manufactured according to the method of the present invention was stable enough even after one month.

The drug product manufactured by freeze-drying the high-concentration solution of the compound (I) according to the present invention is excellent in that good solubility and stability is assured not only just after the preparation but also after the passage of long time.

The same results are also expected in the case of potassium hydroxide and tri-sodium phosphate as well as in the case of sodium hydroxide.

DESCRIPTION OF THE INVENTION

To accomplish the purpose of the present invention, at least one selected from tri-sodium phosphate, a hydrate thereof, sodium hydroxide or potassium hydroxide is used as a pH adjuster. Sodium hydroxide, tri-sodium phosphate or a hydrate thereof or a mixture thereof is preferable and sodium hydroxide is particularly preferable.

For the preparation of the solution comprising exclusively water as a solvent, when the pH adjuster is added, then the preferable pH range of the solution is between 7.0 and 8.5, more preferably between 7.55 and 8.10.

For the preparation of the solution comprising both water and an organic solvent as solvents, when the pH adjuster is added, then the preferable pH range of the solution is between 7.0 and 9.0. Since the pH varies depending upon the amount of organic solvents, the preferable amount of the pH adjuster to add is 4.0~7.0 w/w % of the compound (I), more preferably 4.5~6.0 w/w % in case of sodium hydroxide.

These are added as a solid or as an aqueous solution.

As organic solvents in order to give a solution of higher concentration, alcohol is preferable, ethanol, isopropanol and t-butanol are more preferable, and ethanol is particularly preferable.

The amount of the solvent is preferably 1~40 v/v % of the total solution amount, more preferably 10~40 v/v %, particularly preferably 20–35 v/v %.

The above determines the amount of solvent by volume, but it may be converted into weight by multiplying density (d). For example in using ethanol, when d is assumed 0.785 g/mL, 1 v/v % equals to 0.785 w/v %, 40 v/v % equals to 31.4 w/v %.

The compound (I) may be prepared according to known methods, for example, the method described in JP kokai hei 5-194366 or JP kokai hei 9-40692.

The present invention includes a freeze-dried drug product comprising the compound (I) and at least one pH adjuster selected from tri-sodium phosphate, a hydrate thereof, sodium hydroxide or potassium hydroxide.

Generally, during the manufacturing process of freeze-dried drug products, the drug substance must be kept in a clear solution. That is because suspension and emulsion do not give a stable concentration of the drug substance therein, and furthermore the nozzles of the filling equipment may be stuck up. The present invention gives a clear solution having improved solubility, so that freeze-dried drug products may be manufactured with ease.

The doses to be administered of the compound (I) are determined depending upon age, body weight, symptom, the desired therapeutic effect, the route of administration, and the duration of the treatment. In the human adult, the doses between 100 mg and 1500 mg per person are generally administered by continuous administration between 1 and 24 hours per day from vein. Of course the doses to be used depend upon various conditions. Therefore, there are cases in which doses lower than or greater than the ranges specified above may be used.

For the administration of the compound of the present invention, it may be used as an injection for parenteral administration. Injections for parenteral administration include solutions, solid compositions to be dissolved before administration, e.g. freeze-dried products.

To the drug product of the present invention are optionally added excipients. Preferable excipients include lactose, glucose, maltose, mannitol, xylitol, solbitol, sodium chloride, etc. but in terms of freeze-dried cake, mannitol is more preferably used.

The drug products of the present invention may further include, stabilizing agents, pain-reducing agents, buffering agents and preserving agents, etc.

The drug products of the present invention are sterilized in the final process or prepared by aseptic operation. The freeze-dried products may be dissolved in sterilized distilled water or other solvents (e.g. physiological saline) for injection before use.

Effect of the Invention

The present invention provides a solution comprising water as a solvent having more solubility than a standard by improving the solubility of an insoluble drug compound (I) by adding at least one pH adjuster selected from tri-sodium phosphate, a hydrate thereof, sodium hydroxide or potassium hydroxide, and therewith providing some kinds of drug products using the solution. Moreover the present invention provides a solution of higher concentration by using a mixture of water and an organic solvent as a solvent and a high-dosage drug product using the solution.

Furthermore, the present invention provides a high-concentration solution by using the mixture of water and an organic solvent, and high-dosage products using the solution.

The drug product manufactured by freeze-drying the solution of the compound (I) assures good solubility and stability not only just after preparation but also after long-term storage.

In conventional processes, a relatively large vial was required for manufacturing a high-dosage unit. If the high-concentrated solution prepared by improving the solubility of compound (I) with respect to the solvent, for example, is freeze dried, a high-dosage unit in a smaller vial can be manufactured. As a result, the solution does not require the relatively large vials to provide high dosages, thus reducing cost.

When the compound (I) is administered to a patient of acute pulmonary disorders, for example by intravenous drips, the high-dosage drug product of the present invention alleviates the burden of those engaged in medical care (for example, preparing liquids for injection every several hours before administration, treating plural vials at the same time, etc.). Furthermore, good solubility of the drug product manufactured by the present invention in water enables them to treat the drug product with ease.

BRIEF DESCRIPTION OF DRAWINGS

FIG. 1 is a graph which shows the relationship between pH and the solubility and stability of the compound (I). Circles show the solubility and triangles show the residual rate.

BEST MODE FOR CARRYING OUT THE INVENTION

The following examples illustrate the present invention, but it is not limited to the examples.

EXAMPLE 1(a)

Mannitol (20 g) was dissolved in distilled water, and to the mixture was added the compound (I) (10 g). To the mixture under stirring by a stirrer was added sodium hydroxide (0.44 g) and thereto was added a distilled water to fill up to 500 mL to give a clear aqueous solution of pH 7.65.

EXAMPLE 1(b)

The aqueous solution prepared in example 1(a) was sterilized by a conventional method, filled in vials (5 mL portion each), freeze-dried by a conventional method to give 100 vials each containing 100 mg of the compound (I).

EXAMPLE 2(a)

To the mixture of ethanol (50 mL) and water (total approximately 120 mL) were added the compound (I) (16 g) and mannitol (14 g) and to the mixture under stirring was added 1N aqueous solution of sodium hydroxide (20 mL; corresponds to 800 mg) little by little. To the mixture was added water in order to fill up to 200 mL of total amount to give a clear solution of pH 8.05.

EXAMPLE 2(b)

The aqueous solution prepared in example 2(a) was sterilized by a conventional method, filled in vials (5 mL portion each) and freeze-dried by a conventional method to give 40 vials of freeze-dried drug products each containing 400 mg of the compound (I).

EXAMPLE 3(a)

To the mixture of ethanol (66 mL) and water (total approximately 120 mL) was added the compound (I) (20 g) and mannitol (10 g), and to the mixture under stirring was added 1N aqueous solution of sodium hydroxide (25 mL; corresponds to 1 g) little by little. Thereto was added water in order to fill up to 220 mL in total to give a clear solution of pH 8.09.

EXAMPLE 3(b)

The aqueous solution was sterilized by a conventional method, filled in vials (each 4.4 mL portion) and freeze-dried by a conventional method to give 50 vials each containing 400 mg of the compound (I).

EXAMPLE 4(a)

To a mixture of ethanol (50 mL) and water (total approximately 120 mL) were suspended the compound (I) (14.6 g) and mannitol (14 g) and to the mixture under stirring was added 1N aqueous solution of sodium hydroxide (18 mL; corresponds to 720 mg) little by little. To the mixture was added water in order to fill up to 200 mL of total amount to give a clear aqueous solution of pH 8.04.

EXAMPLE 4(b)

The aqueous solution prepared in example 4(a) was sterilized by a conventional method, filled in vials (5 mL portion each) and freeze-dried by a conventional method to give 40 vials of freeze-dried drug products each containing 366 mg of the compound (I) per each vial.

EXAMPLE 5(a)

To a mixture of ethanol (60 mL) and water (total approximately 120 mL) were suspended the compound (I) (14.6 g) and mannitol (14 g) and to the mixture under stirring was added 1N aqueous solution of sodium hydroxide (18 mL; corresponds to 720 mg) little by little. To the mixture was added water in order to fill up to 200 mL of total amount, to give a clear solution of pH 8.08.

EXAMPLE 5(b)

The aqueous solution prepared in example 5(a) was sterilized by a conventional method and filled in vials (5 mL portion each), freeze-dried by a conventional method to give 40 vials of freeze-dried drug products each containing 366 mg of the compound (I).

EXAMPLE 6(a)

To the mixture of ethanol (66 mL) and water (total approximately 120 mL) were added the compound (I) (18.3 g) and mannitol (10 g) and to the mixture under stirring was added 1N aqueous solution of sodium hydroxide (22. 5 mL; corresponds to 900 mg) little by little. Thereto was added water in order to fill up to 220 mL of the total solution to give a clear solution of pH 8.08.

EXAMPLE 6(b)

The solution prepared in example 6(a) was sterilized by a conventional method, filled to vials (4.4 mL portion each), freeze-dried by a conventional method to give 50 vials of freeze-dried drug products each containing 366 mg of the compound (I).

What is claimed is:

1. A freeze-dried product prepared using a solution, said solution comprising N-[o-(p-pivaloyloxybenzenesulfonylamino)benzoyl]glycine monosodium salt tetra-hydrate of formula (I)

and at least one pH adjuster selected from tri-sodium phosphate, a hydrate thereof, sodium hydroxide or potassium hydroxide, wherein the pH of the solution is 7.0–9.0.

2. A freeze-dried product according to claim 1, wherein exclusively water is used as a solvent.

3. A freeze-dried product according to claim 2, wherein the pH of the solution is 7.0–8.5.

4. A freeze-dried product according to claim 2, wherein sodium hydroxide is used as the pH adjuster.

5. A freeze-dried product according to claim 1, wherein a mixture of water and an organic solvent is used as a solvent.

6. A freeze-dried product according to claim 5, wherein sodium hydroxide is used as a pH adjuster.

7. A freeze-dried product according to claim 5, wherein the organic solvent is alcohol.

8. A freeze-dried product according to claim 7, wherein the organic solvent is ethanol.

9. A drug product manufactured using the freeze-dried product of claim 5.

10. A drug product according to claim 9, which is an injection.

11. A freeze-dried product according to claim 2, wherein said salt of formula (I) is present in a concentration of greater than 6 mg/ml.

12. A freeze-dried product according to claim 2, wherein said salt of formula (I) is present in a concentration of at least 15 mg/ml.

13. A method for the treatment of acute pulmonary disorders comprising administering to a patient an effective amount of a freeze-dried product according to claim 1.

14. A freeze-dried product according to claim 5, wherein said salt of formula (I) is present in a concentration greater than 6 mg/ml.

15. A freeze-dried product according to claim 5, wherein said salt of formula (I) is present in a concentration of at least 15 mg/ml.

* * * * *